(12) United States Patent
Douglas

(10) Patent No.: US 9,558,648 B2
(45) Date of Patent: Jan. 31, 2017

(54) APPARATUS AND METHOD FOR MONITORING HYGIENE

(71) Applicant: Simoniz USA, Inc., Bolton, CT (US)

(72) Inventor: Joel S. Douglas, Groton, CT (US)

(73) Assignee: Simoniz USA, Inc., Bolton, CT (US)

( * ) Notice: Subject to any disclaimer, the term of this patent is extended or adjusted under 35 U.S.C. 154(b) by 0 days.

(21) Appl. No.: 14/479,632

(22) Filed: Sep. 8, 2014

(65) Prior Publication Data

US 2015/0070174 A1   Mar. 12, 2015

Related U.S. Application Data

(60) Provisional application No. 61/875,133, filed on Sep. 9, 2013.

(51) Int. Cl.
*G08B 23/00* (2006.01)
*G08B 21/24* (2006.01)
*G06F 19/00* (2011.01)

(52) U.S. Cl.
CPC .......... *G08B 21/245* (2013.01); *G06F 19/327* (2013.01)

(58) Field of Classification Search
CPC .. G08B 21/245; G06F 19/3418; G06F 19/327; A61B 5/1122; G07C 1/10; G05B 1/01
USPC ............... 340/539.13, 539.1, 539.12, 501, 10.1,340/573.1, 541, 573.4, 500, 529, 539.11, 603
See application file for complete search history.

(56) References Cited

U.S. PATENT DOCUMENTS

| | | | |
|---|---|---|---|
| 4,135,561 A | 1/1979 | Senelonge | |
| 4,722,372 A | 2/1988 | Hoffman et al. | |
| 4,986,144 A | 1/1991 | Kobayashi et al. | |
| 5,202,666 A * | 4/1993 | Knippscheer | G08B 21/245 340/541 |
| 5,226,462 A | 7/1993 | Carl | |
| 5,476,194 A | 12/1995 | Hippely et al. | |
| 5,492,247 A | 2/1996 | Shu et al. | |
| 5,670,945 A | 9/1997 | Applonie | |
| 5,683,012 A | 11/1997 | Villaveces | |
| 5,819,986 A | 10/1998 | Last et al. | |
| 5,927,548 A | 7/1999 | Villaveces | |
| 5,945,910 A | 8/1999 | Gorra | |
| 6,347,414 B2 * | 2/2002 | Contadini | 4/222 |
| 6,727,818 B1 * | 4/2004 | Wildman | G06F 19/3418 340/10.1 |
| 7,372,267 B2 | 5/2008 | Bieri et al. | |

(Continued)

*Primary Examiner* — Hoi Lau
(74) *Attorney, Agent, or Firm* — McCormick, Paulding & Huber LLP

(57) ABSTRACT

Method and apparatus for monitoring and reporting hand washing at a sanitizing station employs a sensor for signaling the dispensing of a sanitizer from a dispenser and a sensor module detecting the direction of passage of an individual into and out of a portal, such as the entrance to a sanitary area. The apparatus operates in a normal mode and a bypass mode. In the normal mode, the apparatus responds to the sensor indicating that an individual has not dispensed sufficient sanitizer to mitigate the spread of germs from care giver/health care worker to patient, and sounds an alarm when the individual passes through the portal in a particular direction, for example into or out of the sanitary area. Separate signals can be generated and recorded for each direction of passage through the portal. In the bypass mode, the alarm is not sounded and allows passage into and out of the sanitary area when a sanitary condition is not needed.

26 Claims, 4 Drawing Sheets

(56) References Cited

U.S. PATENT DOCUMENTS

| | | | |
|---|---|---|---|
| 7,372,367 B2 | 5/2008 | Lane et al. | |
| 7,375,640 B1* | 5/2008 | Plost | A47K 5/1217 340/500 |
| 8,502,681 B2* | 8/2013 | Bolling | G06F 19/327 340/539.1 |
| 2001/0032353 A1* | 10/2001 | Contadini | E03D 9/002 4/222 |
| 2003/0030562 A1* | 2/2003 | Lane | G08B 21/245 340/573.4 |
| 2004/0090333 A1* | 5/2004 | Wildman | G06F 19/3418 340/573.1 |
| 2006/0005312 A1* | 1/2006 | Reddy | A47K 13/24 4/668 |
| 2007/0096930 A1* | 5/2007 | Cardoso | G08B 21/245 340/573.4 |
| 2008/0087719 A1* | 4/2008 | Sahud | G08B 21/245 235/376 |
| 2008/0246599 A1* | 10/2008 | Hufton | G01S 1/70 340/529 |
| 2009/0051545 A1* | 2/2009 | Koblasz | G08B 21/245 340/573.1 |
| 2009/0091458 A1* | 4/2009 | Deutsch | G06F 19/327 340/573.1 |
| 2009/0119142 A1* | 5/2009 | Yenni | G06Q 10/06 705/7.15 |
| 2009/0224907 A1* | 9/2009 | Sinha | G08B 21/245 340/539.11 |
| 2010/0117836 A1* | 5/2010 | Seyed Momen | G01S 1/70 340/573.1 |
| 2010/0164728 A1* | 7/2010 | Plost | G08B 21/245 340/573.1 |
| 2010/0315244 A1* | 12/2010 | Tokhtuev | G06Q 10/00 340/603 |
| 2011/0057799 A1* | 3/2011 | Taneff | G06F 19/327 340/573.1 |
| 2011/0148586 A1* | 6/2011 | Anderson | G06F 19/327 340/10.1 |
| 2011/0163870 A1* | 7/2011 | Snodgrass | A61B 5/1122 340/539.11 |
| 2011/0227740 A1* | 9/2011 | Wohltjen | G06F 19/327 340/573.1 |
| 2011/0273298 A1* | 11/2011 | Snodgrass | G08B 21/245 340/573.1 |
| 2011/0291841 A1* | 12/2011 | Hollock | G08B 21/245 340/573.1 |
| 2012/0194338 A1* | 8/2012 | Snodgrass | G08B 21/245 340/539.12 |
| 2012/0256742 A1* | 10/2012 | Snodgrass | G06F 19/327 340/539.12 |
| 2013/0015956 A1* | 1/2013 | Wegelin | G07C 1/10 340/10.1 |
| 2013/0113619 A1* | 5/2013 | Snodgrass | G07C 11/00 340/539.11 |
| 2013/0122807 A1* | 5/2013 | Tenarvitz | H04B 5/0031 455/41.1 |
| 2013/0127615 A1* | 5/2013 | Snodgrass | G05B 1/01 340/539.13 |
| 2013/0229263 A1* | 9/2013 | Graczyk | G01S 1/70 340/10.1 |
| 2013/0229276 A1* | 9/2013 | Hunter | G08B 21/245 340/501 |
| 2013/0342349 A1* | 12/2013 | Cruz | G08B 21/245 340/573.1 |
| 2014/0247125 A1* | 9/2014 | Barsky | G06F 19/327 340/539.12 |
| 2015/0048940 A1* | 2/2015 | Keown | G06F 19/327 340/539.12 |
| 2015/0070174 A1* | 3/2015 | Douglas | G08B 21/245 340/573.1 |
| 2015/0206077 A1* | 7/2015 | Himmelmann | G06Q 10/063118 340/870.07 |
| 2015/0228181 A1* | 8/2015 | Himmelmann | G08B 21/245 340/573.1 |
| 2015/0254965 A1* | 9/2015 | Moore | G08B 21/245 340/539.12 |

\* cited by examiner

APPARATUS AND METHOD FOR MONITORING HYGIENE

CROSS-REFERENCE TO RELATED APPLICATIONS

This application claims the benefit of U.S. Provisional Patent Application No. 61/875,133 filed Sep. 9, 2013, which is incorporated herein by reference in its entirety.

FIELD OF THE INVENTION

This invention relates to methods and apparatus for promoting hygiene, and more particularly, for promoting frequent sanitization and hand washing by personnel in facilities such as hospitals, healthcare facilities, foodservice facilities, and restaurants, and by other personnel in frequent contact with the public.

BACKGROUND OF THE INVENTION

Discovery of penicillin during the middle of the twentieth century, and the development and widespread use of other antibiotics in the decades since, have been of tremendous benefit in curtailing the spread of infectious disease. Doubtless, antibiotics save lives and help avoid innumerable debilitating incidents of infection. However, as with many scientific advances, there are also limits. Reliance on antibiotics corresponds to an unfortunate de-emphasis of other simple and highly effective means of controlling bacteria, such as frequent sanitizing. Furthermore, the prevalent use, and perhaps over prescription, of antibiotics has lead to a natural selection process that favors those bacteria least affected by the antibiotics. Strains of bacteria are appearing that are highly resistant to many common antibiotics.

Concern with avoiding the spread of infectious disease is particularly high in those industries that deal with the public, such as the healthcare and food service industries. A single person, as a result of one incident of carelessness, such as not washing after using the bathroom, can transmit infectious bacteria to any number of patrons. The results can be disastrous, not only to those infected, but also to the employer's business and reputation. Because the public interest is clearly at issue, the Food and Drug Administration has promulgated regulations that address washing by hospital, foodservice and other personnel. FDA regulations identify hand washing as a "critical item", such that violations of the rules governing hand washing "are more likely than other violations to lead to food contamination, illness, or environmental degradation". The FDA regulations further specify that personnel must wash twice after using the bathroom, using a specified wash procedure. The regulations also require that "a person in charge routinely monitor person hand washing to ensure that persons are effectively washing their hands".

Of course, compliance with hygiene standards must be complete to minimize the chance of the transmission of infection. The failure of one worker to properly sanitize his or her hands can negate the efforts of all other workers who have been careful to properly sanitize their hands before touching patients or handling food. Ensuring complete compliance requires constant diligence on the part of supervisors, who typically have other pressing duties that can distract them from always effectively monitoring the hygiene of persons. Accordingly, there are known in the art systems for automating oversight and record keeping of person hand washing.

For example, U.S. Pat. No. 5,202,666 is directed to ensuring proper person hand washing. Persons are monitored, and carry a receiver and transmitter, preferably in the form of a badge. A multitude of transmitters, receivers and transducers, as well as proximity detectors, switches, valves and a computer, ensure that various activities relating to hand washing, such as dispensing water or soap or activating a blower, do actually occur. An alert signal is generated if the apparatus determines that an individual fails to properly wash, activating a light on the person's badge, reporting to a central computer or otherwise providing a warning.

U.S. Pat. No. 4,986,144 relates to a warning system using a door-activated switch. The switch detects entry to a wash facility, and an alarm warns the person entering to wash their hands prior to leaving or entering. When used in a bathroom, the warning system can be activated by the flushing of toilet, and can lock the door to ensure that the person properly washes their hands before leaving.

As another example, the system described in U.S. Pat. No. 5,670,945 uses two moisture-proof switches for sensing the immersion of both hands of the person in an antiseptic solution. Proximity detectors are installed to sense when a person approaches and moves away from a special wash station adjacent a food handling area. The system activates an alarm if a logic unit determines that a person has approached the washbasin and entered the food handling area without immersing both hands in the antiseptic solution.

U.S. Pat. Nos. 5,683,012, and 5,927,548, describe a novel, body-worn dispenser for alcohol-glycerin disinfectant gel that doctors and nurses can use to disinfect their hands before and after patient contacts. These patents do not disclose any means to monitor, track or record the usage dose applications of the disinfecting gel dispenser nor do they disclose any means for its piston pump which can be variably actuated depending on the amount of pressure applied by the user's hand, to dispense exact dose applications of the disinfecting gel.

U.S. Pat. No. 5,476,194 and U.S. Pat. No. 5,819,986, both describe personal, portable, and refillable fluid dispensers. U.S. Pat. No. 5,476,194 describes an attachment means for a dispenser device to be worn on the body of the user. U.S. Pat. No. 5,819,986 describes a piston action pump to deliver an amount of fluid. Neither of these patents disclose any method or apparatus to provide uniform unit dose applications of the fluid dispensed or methods to monitor, track, record and report usage information of a fluid dispenser.

U.S. Pat. No. 5,945,910 describes a method and apparatus for monitoring and reporting hand washing, and U.S. Pat. No. 5,670,945 describes a self-monitoring, hand-sanitizing station. U.S. Pat. No. 5,202,666 describes a method and apparatus for enhancing hygiene. The preceding three (3) patents refer in general to a non-portable wash station that many people access to wash their hands. Each patent describes separate novel methods and apparatus to monitor, record and report various hand washing activity that occurs at a given wash station.

U.S. Pat. No. 5,492,247 describes a fluid reservoir that is replaceable from a rigidly mounted dispenser utilized by many users. U.S. Pat. No. 4,722,372 further describes a dispenser for multiple user access with a disposable fluid reservoir.

U.S. Pat. No. 5,226,462 discloses a unique method and apparatus to accurately introduce measured amounts of liquid into receptacles. Additionally, U.S. Pat. No. 4,135,561 describes a similar method and apparatus for filling vials in an automated system.

U.S. Pat. No. 7,372,267 discloses a method of measuring hand hygiene compliance the includes the steps of maintaining a computer database and determining whether any person entered a first area independent of whether the any person includes a sensor.

U.S. patent application Ser. No. 12/042,699 discloses a method of tracking sanitization and an alarm system that automatically monitors hand sanitizing.

U.S. patent application Ser. No. 12/684,034 discloses a method of tracking sanitization and an alarm system that is in communication with a dispenser for sanitizing agent and automatically monitors if the individual has dispensed sanitizing agent prior to entering or leaving a monitored area.

Although there are a considerable number of patents issued for dispensing apparatus and methods, there does not appear to be any prior art which directly relates to the monitoring of the amount of sanitizer dispensed and associates the dispensing with the crossing of the monitored portal. Also the ability for a monitor to determine if the person is entering or leaving a room is important due to the sanitizing requirements are different for someone entering a room versus someone leaving a room. The monitor is also configured so that a minimal amount of fluid must be dispensed from an associated dispenser to confirm the dispensing.

SUMMARY OF THE INVENTION

Unfortunately, known systems can be relatively complex, and there is a need for a system which provides feed back for a person to remind them that they need to sanitize their hands prior to passing through a portal, such as a door entering a patient's room or area that requires hand-sanitizing, such as food prep areas. Accordingly, it is an object of the present invention to provide a method and apparatus for monitoring and thereby promoting hand hygiene.

A second aspect of the invention in the hospital environment is associated with cost control. The invention addresses this major concern by providing an easy-to-implement retrofit for existing hand-sanitizing systems. The stand-alone nature of the invention makes it easy to implement. Another object of the invention is to provide a method and apparatus for monitoring that can distinguish between personnel entering and leaving the room through a portal.

Yet another object of the invention, is to provide a means to monitor the quantity of sanitizer that has been dispensed from the dispenser.

The monitoring apparatus is activated by a person when they dispense a sufficient amount of sanitizer to thoroughly sanitize their hands. This is significant because many times a person does not dispense a sufficient amount of sanitizer which in turn does not adequately sanitize their hands. Such monitoring is accomplished by locating a sensor switch inside of the hand sanitizer that requires the complete depression of the sanitizer dispenser for activation. The activated switch then activates indicator lights that signify that the person has sanitized their hands and may pass through a portal to enter a room. If the person does not activate the dispenser and enters the room, a portal sensor module detects the person entering the room and an alarm will sound. The dispenser switch is set to assure that the dispenser is fully-depressed and ensures that the correct amount of sanitizer is dispensed, or it will not allow access to the room and keep a do-not-enter-light illuminated. By monitoring full depression, the user is prevented from inadequate dispensing and incomplete sanitation practice. The dispenser sensor can be optical, magnetic, mechanical, electronic, or any means that allows for the sensing of an adequate amount of sanitizer to sanitize a person's hands. The sanitizer dispenser can be either manually-activated or auto-device, which dispenses the sanitizer when a hand is presented to the dispenser.

The portal sensor module is configured such that there are two sensors located in the module. The two sensors are selected and positioned so that they can sense the direction of motion of an individual moving pass the monitor through the associated portal. The sensor module is also positioned in the monitor so that it is rotatable and can be positioned through an angular range so as to be adaptable for a wide range of portal configurations. The proposed device can be used either with the alarm or without it, and it can also be configured with or without, a visual display, such as a video display, LCD display, lights or LED lights.

The controller for the apparatus, sensors, sensor module, or indicator device, can be either connected to the sanitizer dispenser by discrete wiring, or through a wireless communication system such as Bluetooth, NFS or WIFI or a proprietary wireless network.

The invention provides an apparatus for monitoring hygiene, comprising: a first sensor in communication with a dispensing device for a sanitizing agent, said sensor being activated when a certain amount of sanitizing agent has been dispensed; a second sensor positioned for automatically detecting when an individual has passed through a portal at an area requiring sanitary conditions, said sensor turning on when the individual has passed through the portal; a third sensor positioned for automatically detecting when an individual has passed through the portal, said sensor turning on when the individual has passed through the portal; a controller in communication with the second sensor and third sensor and logic in the controller that compares the activation times of second sensor and the third sensor, and an alert indicator operatively connected to the controller for generating an alert signal indicating the direction in which an individual has passed through said portal without activation of said first sensor.

The first and second sensor being located on a platform within a housing such that the platform is capable of being rotated about a vertical axis allowing the first and second sensors to be positioned to view the portal and avoid obstructions.

The invention provides a method for monitoring and enhancing hygiene, comprising: providing a first sensor in communication with a dispensing device that dispenses a sanitizing agent; activating the first sensor to produce signals when a sanitizing agent has been dispensed; providing a sensor module to detect when individuals have passed through a portal and producing signals indicating the direction of passage; connecting a controller to the first sensor and the sensor module to receive the signals produced; and causing the controller to generate an alert signal upon detecting that an individual has passed through said portal and has not caused activation of said first sensor; and recording the generation of the alert signal and the direction of passage through the portal.

DETAILED DESCRIPTION OF THE PREFERRED EMBODIMENTS

Figure 1:
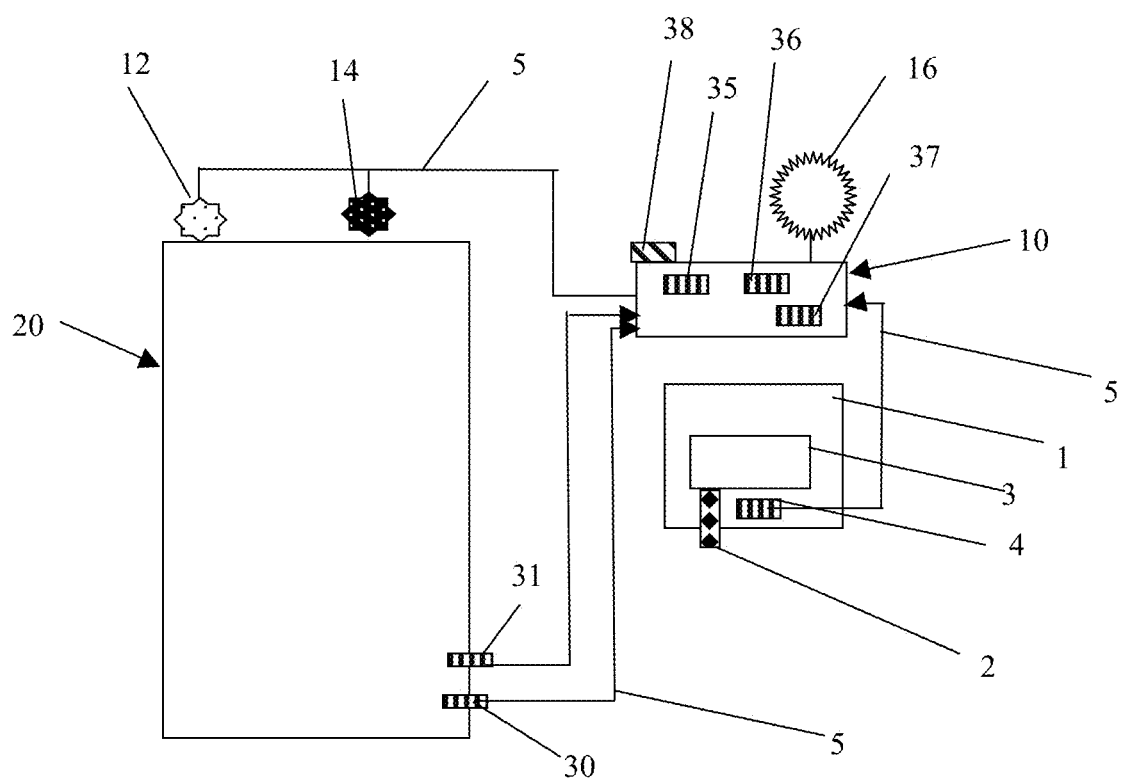
FIG. 1 is a block diagram of the sanitizer monitoring apparatus.

Referring to the hygiene monitoring apparatus in FIG. 1, a fluid dispenser 1 is either a hand-operated or auto-dispense type dispenser of a liquid or semi-liquid (gel) sanitizer. The dispenser comprises an ejection nozzle 2, a sanitizer reservoir 3, dispensing sensor 4, and signal device 5. Signal device 5 can be a wired connector, WIFI signal, or proprietary wireless signal. Dispensing sensor 4 can be selected from switches that are mechanical, magnetic, infrared, passive-infrared, optical, infrared, conductive, or pressure activated.

The ejection nozzle 2 is positioned to dispense a liquid, foam, or gel sanitizer from the sanitizer reservoir 3 when the dispenser is activated. The activation can be either manual or automatic upon the sensing of a hand under the nozzle 2.

A programmed controller 10 receives the dispensing signal from dispensing sensor 4 via the signal device 5, provided that at least a specific quantity of sanitizer has been dispensed for the sanitation to be accomplished. If the dispensing sensor 4 is activated the controller 10 extinguishes a "do-not-pass" indicator 12 and illuminates the "able-to-pass" indicator 14 for a specific amount of time which indicates that the person can pass through the portal 20 to hospital room, food preparation area, or other area to be kept sanitary. After the specific amount of time has expired the controller 10 extinguishes the "able-to-pass" indicator 14 and illuminates the "do-not-pass" indicator 12.

If a person enters the portal 20 without activating the dispensing sensor 4, and a first portal sensor 30 senses the person before a second portal sensor 31, the controller 10 causes the "do-not-pass" signal 12 to be illuminated, and alarm 16 to be activated. The alarm 16 reminds the person entering the room or other sanitary area that they need to sanitize their hands. Alarm 16 can be any audible indicator that meets the requirements of the installation such as ring-tone, buzzer, beep, or voice. If the portal sensor 30 senses the person after portal sensor 31, the different sequence of signals from the portal sensors produces different results described hereafter in conjunction with FIGS. 2 and 3. The portal sensors 30 and 31 can be selected from switches that are mechanical, ultra-sonic, magnetic, optical, infrared, passive-infrared, conductive, pressure-activated, or mechanical electronic.

The system can also be configured so that it has a bypass mode that is activated by bypass switch 35. For example, hospital personnel may manually set the bypass switch in the bypass mode to allow equipment and beds to be moved in and out of the area without the alarm 16 being activated.

The counter switch 36 allows authorized personnel to access the counters so that statistical information can be collected from the controller 10. The access may also be gained by a direct communication from a computer by way of a USB, Bluetooth, NFS, serial or parallel communication port 37.

Figure 2:
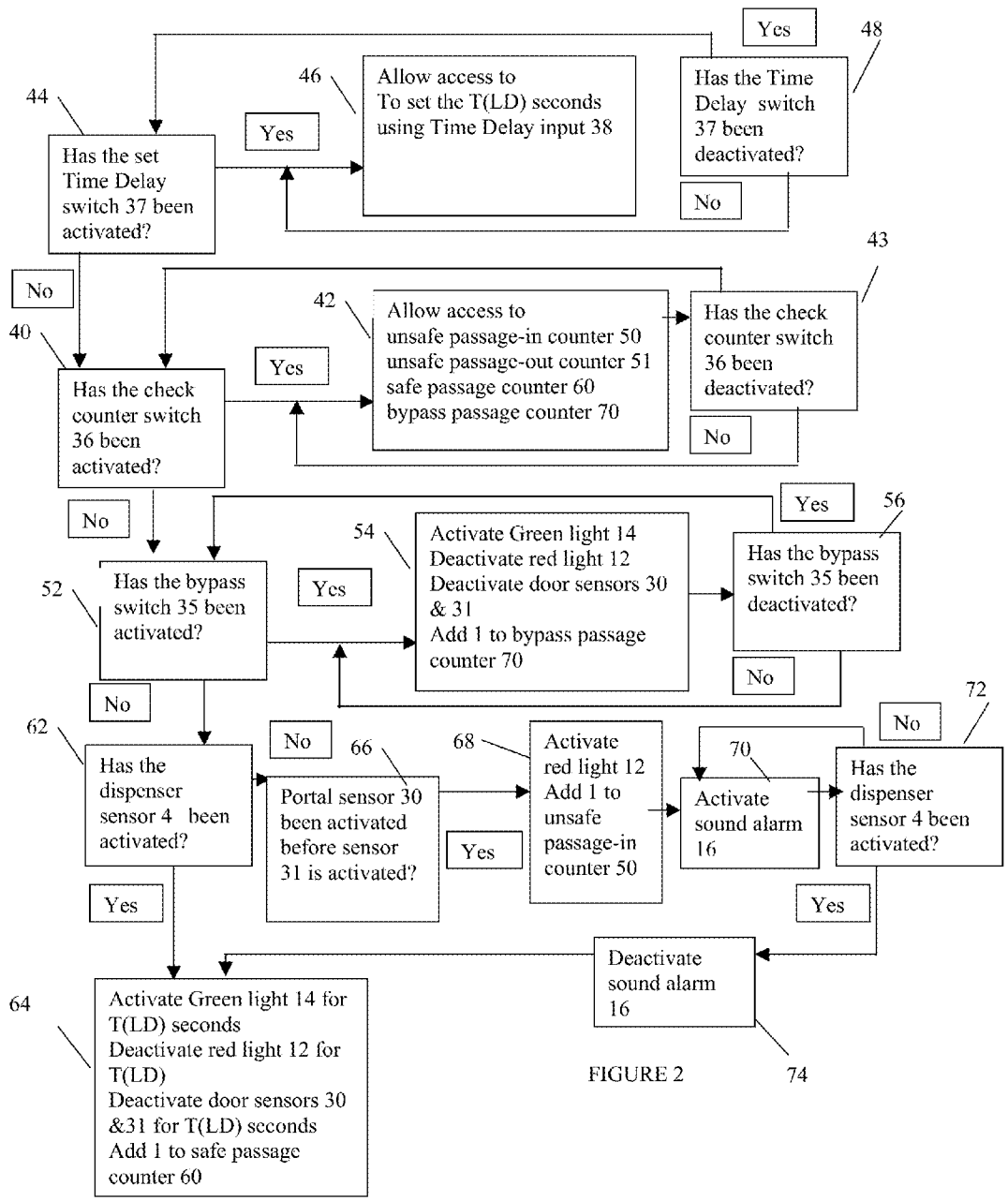
FIG. 2 is a flow-chart of the algorithm in controller of the apparatus.
Figure 3:
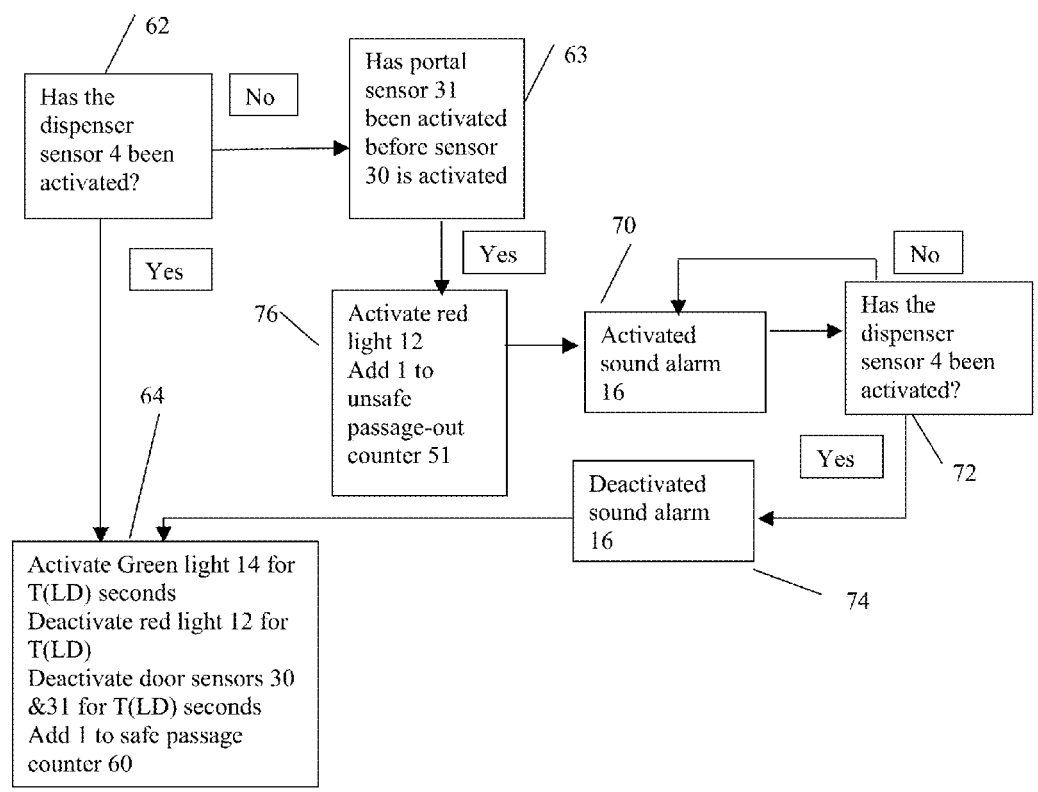
FIG. 3 is an additional subroutine in the algorithm of the controller.

Referring to FIG. 2, and FIG. 3 a flow chart showing the logic of the controller algorithm according to one aspect of the invention is shown. If the counter switch 36 has been activated as queried at box 40, the controller 10 allows access to the unsafe passage-in counter 50, unsafe passage-out counter 51, safe passage counter 60, bypass passage counter 70, as shown a box 42, until the counter switch 36 is deactivated at box 43. During that time the counters can be down-loaded and/or zeroed by the authorized staff. The counter switch 36 can be electronic entry, key switch, or recessed button switch, which minimizes or eliminates unauthorized activation. If the Time Delay switch 37 has been activated as queried at box 44, then the authorized staff can reset the time delay for the portal entrance time as shown at box 46, until the switch is deactivated as shown at box 48. This can be accomplished by direct communication with the controller, or by adjusting the Time Delay input 38 which can be a potentiometer, push button switches, rotary switches, or any other means of communicating with the controller the amount of time for the delay.

If the bypass switch 35 has been activated by authorized staff at box 52, then the controller will Activate Green light 14, Deactivate Red light 12, Deactivate portal sensor 30 and portal sensor 31, and Add 1 to bypass passage counter 70 as indicated at box 54 until the bypass switch 35 been deactivated as indicated at box 56.

If the dispenser sensor 4 has been activated in the course of dispensing sanitizer and the sensors 30, 31 have been activated by an individual passing through the portal, as queried at box 62, the controller 10 will then set the Activate Green light 14 on for T(LD) seconds, Deactivate red light 12 for T(LD), Deactivate portal sensor 30 and portal sensor 31 for T(LD) seconds, and Add 1 to safe passage counter 60 as shown at box 64.

The hygiene monitoring apparatus of FIG. 1 is also designed to insure that persons entering and exiting the sanitary area through the portal 20 are reminded to use the sanitizing dispenser 1. If the dispenser sensor 4 has not been activated by the dispensing of sanitizer, and the portal sensor 30 has been activated before the portal sensor 31 is activated, as queried at box 66, both of which indicate someone has entered the sanitized area through the portal 20 without using the sanitizing dispenser, the controller 10 will Activate red light 12, Add 1 to unsafe passage-in counter 50, and sound alarm 16 as indicated at box 68 warning the person entering that he must sanitize, until the dispenser sensor 4 been activated. Upon activation of the sanitizer dispenser, and detection by sensor 4 as indicated at box 70, the alarm is deactivated at box 72, and the green "able-to-pass" light 14 is activated as shown at box 64.

Figure 4:
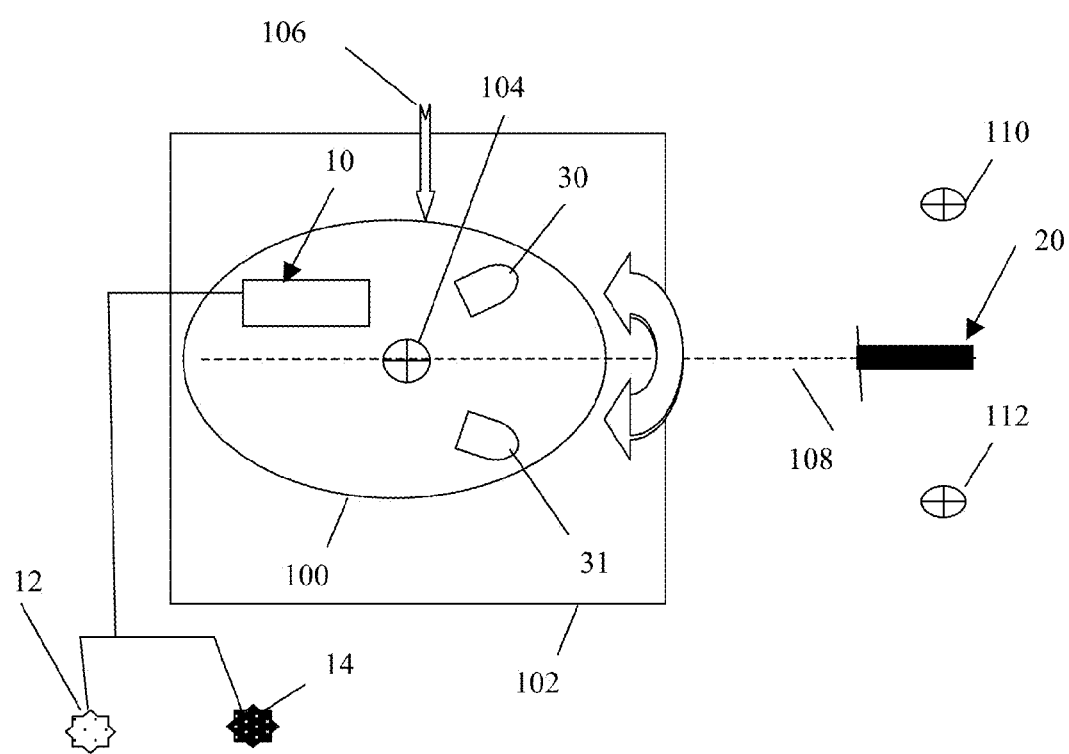
FIG. 4 is a schematic diagram of the structure supporting the sensor module.

In the design layout of the apparatus in the schematic diagram of FIG. 4, the sensors 30 and 31 are shown installed on a platform 100 in a fixed outer housing 102 next to the portal 20. The platform with the sensors is rotatable about a vertical axis 104 as indicated by the double arrow. The housing has a locking mechanism 106, such as a set screw, which when engaged locks the platform 100 in a fixed orientation relative to outer housing 102 and the portal 20. The sensors 30 and 31 when rotated about axis 104 can be set to any angle with respect reference line 108 that extends across the portal from one side to the other. The angle of rotation can be selected from 0 to 181 degrees. This allows sensors 30 and 31 to be aligned with any portal that the monitor is installed to observe.

The sensors 30 and 31 preferably are installed on the platform 100 in the housing 102 such that sensor 30 is located to one side of the reference line 108, and the sensor 31 is located on the opposite site of the line 108. The sensor 30 is oriented 1 to 10 degrees away from the center of the portal so that it is aimed toward a target 110 lying outside the sanitary area. The sensor 31 is oriented from 1 to 10 degrees away from the center of the portal 20 so that it is aimed toward target 112 inside the sanitary area, and its field of view does not intersect the field of view of the sensor 30.

This configuration will allow the sensors to determine if a person is entering or leaving the sanitary area. If the sensor 30 is activated before the sensor 31 by a person entering the sanitary area through the portal 20 without using the dispenser 1, the unsafe passage-in is indicated at box 68 and the alarm is sounded as indicated at box 70 in FIG. 2. When the person hears the alarm and responds by using the sanitary dispenser 1, the alarm and lights are deactivated or activated accordingly as indicated at boxes 72, 74, and 64. If the sensor 31 is activated before the sensor 30 by a person leaving the sanitary area through the portal 20 as queried at box 63 in FIG. 4, the unsafe passage-out is indicated at box 76 and the alarm is sounded as indicated at box 70. If desired, a short time delay can be introduced before box 76 to allow an exiting person to activate the sanitary dispenser and avoid an alarm and recording of an unsafe exit from the sanitary area. The use of the sanitary dispenser upon exiting is desirable to prevent the transmission elsewhere of germs or bacteria that may be present in the area.

Therefore, while the invention has been illustrated and described in detail in the drawings and foregoing description, the same is to be considered as illustrative and not restrictive in character, it being understood that only the preferred embodiments have been shown and described and that all changes and modifications that come within the spirit and scope of the following claims and equivalents are desired to be protected.

What is claimed is:

1. An apparatus for monitoring hygiene, comprising:
a dispensing device positioned outside an area requiring sanitary conditions for dispensing a sanitizer;
a first sensor associated with the dispensing device, said first sensor being activated when sanitizer has been dispensed;
a second sensor disposed to view a portal to the area requiring sanitary conditions for detecting when an individual has passed through the portal, said second sensor viewing a side of the portal proximal the dispensing device;
a third sensor disposed to view the portal to the area requiring sanitary conditions for detecting when an individual has passed through the portal, said third sensor viewing a side of the portal distal the dispensing device; and
a programmed controller connected with said first sensor, the second sensor, and third sensor;
the controller having programming logic that compares the activation times of said first, second and third sensors and activates a perceptible able-to-pass signal for a pre-determined period of time after activation of the first sensor, and in the absence of the able-to-pass signal without a time delay produces an alert signal and an unsafe passage signal in case the second sensor is activated before the third sensor, or in case the third sensor is activated before the second sensor, produces an alert signal and an unsafe passage signal after a time delay during which the first sensor has not been activated.

2. The apparatus of claim 1 wherein the first sensor is not activated unless a certain quantity of sanitizer is dispensed.

3. The apparatus of claim 1 further including a counter for storing the number of unsafe passage signals.

4. The apparatus of claim 1 further including a first counter for storing the number of unsafe passages inwardly through the portal and a second counter for storing the unsafe passages outwardly through the portal.

5. The apparatus of claim 1 wherein the controller also produces a safe passage signal when an individual has passed through the portal and has activated the first sensor associated with the dispenser.

6. The apparatus of claim 5 further including a counter for storing the number of safe passage signals.

7. The apparatus of claim 1 wherein said second sensor and third sensor are fixed to a platform and are aimed so that their fields of view do not intersect.

8. The apparatus of claim 7, where the platform is positioned inside a housing so that it is rotatable about an axis.

9. The apparatus recited in claim 1, wherein said first sensor is selected from the group consisting of a mechanical switch, an ultrasonic detector, an optical switch, an infrared detector, a magnetic switch, a pressure-activated switch, and a conductive switch.

10. The apparatus recited in claim 1, wherein said second sensor is selected from the group consisting or a mechanical switch, an ultrasonic switch, an optical switch, an infrared detector, a magnetic switch, a pressure-activated switch, and a conductive switch.

11. The apparatus recited in claim 1, wherein said third sensor is selected from the group consisting or a mechanical switch, an ultrasonic switch, an optical switch, an infrared detector, a magnetic switch, a pressure-activated switch, and a conductive switch.

12. The apparatus recited in claim 1, wherein the first sensor is in wireless communication with the controller with a wireless communication link.

13. The apparatus recited in claim 1, wherein the second sensor is in communication with the controller with a wireless communication link.

14. The apparatus recited in claim 1, wherein the first sensor is in communication with the controller with a wired conductive element.

15. An apparatus for monitoring hygiene practices of personnel, comprising:
a dispensing device for dispensing a sanitizer;
a first sensor associated with the dispensing device, said first sensor being activated when a quantity of sanitizer has been dispensed;
a sensor module for detecting when an individual has passed through a portal and producing signal indicative of the direction of passage through the portal, said sensor module including a second sensor having a view of the portal proximal the dispensing device and a third sensor having a view of the portal distal the dispensing device, said second and third sensors being mounted to a common platform that is rotatable about a vertical axis;
an alarm device;
a controller in communication with the first sensor, the sensor module, and the alarm device, and activating the alarm device and generating an unsafe passage signal indicating an individual has passed through the portal in a specific direction of passage without activating said first sensor.

16. The apparatus of claim 15 wherein the sensor module has two sensors activated in one and an opposite sequence depending upon the direction of passage through the portal.

17. The apparatus of claim 15 wherein the controller has a bypass mode in which the controller is unresponsive to individuals passing through the portal.

18. The apparatus of claim 15 further including a storage device for recording the number of safe passages of individuals through the portal without an unsafe passage signal.

19. The apparatus recited in claim 15 further including a storage device for recording the number of unsafe passage signals.

20. The apparatus recited in claim 19 wherein the storage device includes a counter for recording the number of unsafe passage signals in one direction through the portal.

21. The apparatus recited in claim 20 wherein the storage device includes another counter for recording the number of unsafe passages in the opposite direction through the portal.

22. A method for monitoring and enhancing hygiene, comprising:
   providing a first sensor in association with a dispensing device that dispenses a sanitizer, the sensor being activated to produce a signal when a quantity of sanitizer has been dispensed;
   providing a bi-directional sensing module to detect when an individual has passed through a portal associated with a sanitary area and the direction of passage of the individual through the portal;
   activating a perceptible able-to-pass signal in response to activation of the first sensor prior to passage of an individual through the portal into the sanitary area;
   immediately activating an alarm device in response to the bi-directional sensing module to signal an unsafe passage when an individual passes through the portal into the sanitary area without a signal from the first sensor; and
   activating an alarm device after a time delay in response to the bi-directional sensing module to signal an unsafe passage when an individual passes through the portal exiting the sanitary area without a signal from the first sensor.

23. The method for monitoring as defined in claim 22 further including recording the number of unsafe passages of an individual through the portal in a specific direction.

24. The method for monitoring as defined in claim 22 further including recording the number of unsafe passages of an individual through the portal in one direction, and separately recording the number of unsafe passages of an individual through the portal in the opposite direction.

25. The method recited in claim 22 wherein the first sensor is activated to produce a signal when a specific quantity of sanitizer has been dispensed.

26. The method recited in claim 22 further including recording the number of times an individual passes through the portal with a signal from the first sensor.

* * * * *